(12) United States Patent
Casset

(10) Patent No.: US 7,454,247 B2
(45) Date of Patent: Nov. 18, 2008

(54) DISCRIMINATION OF NOXIOUS AND NON NOXIOUS VENTRICULAR EXTRASYSTOLES IN AN ACTIVE IMPLANTABLE MEDICAL DEVICE SUCH AS A CARDIAC PACEMAKER, DEFIBRILLATOR, CARDIOVERTOR AND/OR MULTISITE DEVICE

(75) Inventor: Cyrille Casset, Paris (FR)

(73) Assignee: ELA Medical S.A.S., Montrouge (FR)

( * ) Notice: Subject to any disclaimer, the term of this patent is extended or adjusted under 35 U.S.C. 154(b) by 568 days.

(21) Appl. No.: 10/679,765

(22) Filed: Oct. 6, 2003

(65) Prior Publication Data
US 2004/0147968 A1 Jul. 29, 2004

(30) Foreign Application Priority Data
Oct. 4, 2002 (FR) .................................. 02 12292

(51) Int. Cl.
*A61N 1/362* (2006.01)
(52) U.S. Cl. ........................................................ 607/9
(58) Field of Classification Search ................ 607/4–28
See application file for complete search history.

(56) References Cited

U.S. PATENT DOCUMENTS

| | | | | |
|---|---|---|---|---|
| 5,168,869 A | * | 12/1992 | Chirife | 607/25 |
| 5,312,451 A | * | 5/1994 | Limousin et al. | 607/15 |
| 5,645,576 A | * | 7/1997 | Limousin et al. | 607/19 |
| 5,792,194 A | * | 8/1998 | Morra | 607/17 |
| 6,052,616 A | * | 4/2000 | Bonnet et al. | 600/515 |
| 6,360,123 B1 | * | 3/2002 | Kimchi et al. | 600/547 |
| 2001/0034540 A1 | | 10/2001 | Molin | 607/20 |

FOREIGN PATENT DOCUMENTS

| | | |
|---|---|---|
| EP | 0 550 342 | 12/1992 |
| EP | 1 138 346 | 3/2001 |

* cited by examiner

*Primary Examiner*—Scott M Getzow
(74) *Attorney, Agent, or Firm*—Orrick Herrington & Sutcliffe, LLP

(57) ABSTRACT

An active implantable medical device, such as a cardiac pacemaker, defibrillator, cardiovertor and/or multisite device, able to discriminate noxious and non noxious ventricular extrasystoles. The device is able to detect a heartbeat rate and detect in the rate an occurrence of a ventricular extrasystole (VES). It also is able to measure an intracardiac impedance (Z), correlated with the instantaneous blood flow, and determine, in response to variations of the impedance signal, the presence or the absence of a significant mechanical activity of the myocardium consecutive to the ventricular extrasystole. In response to such variations, the device provides an indicator of the noxious or non noxious character of the ventricular extrasystole. This indicator allows, inter alia, on the following cycle, to adapt in a differentiated way an operating parameter such as the ventricular escape interval, according to the determined noxious or non noxious character of the ventricular extrasystole.

7 Claims, 1 Drawing Sheet

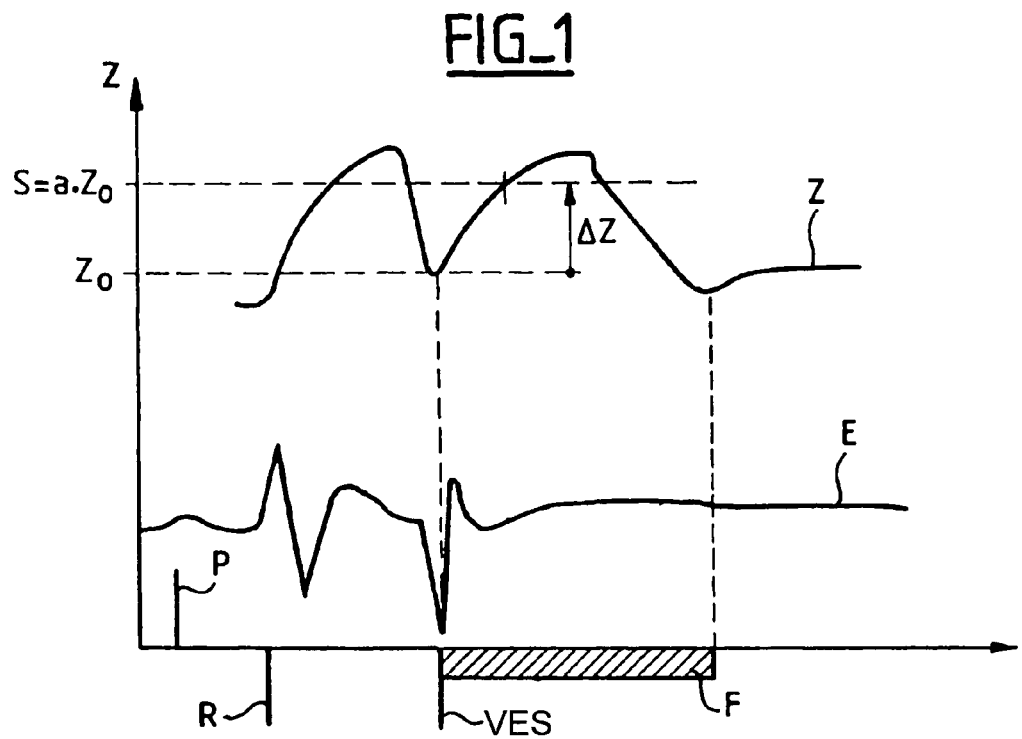
FIG_1
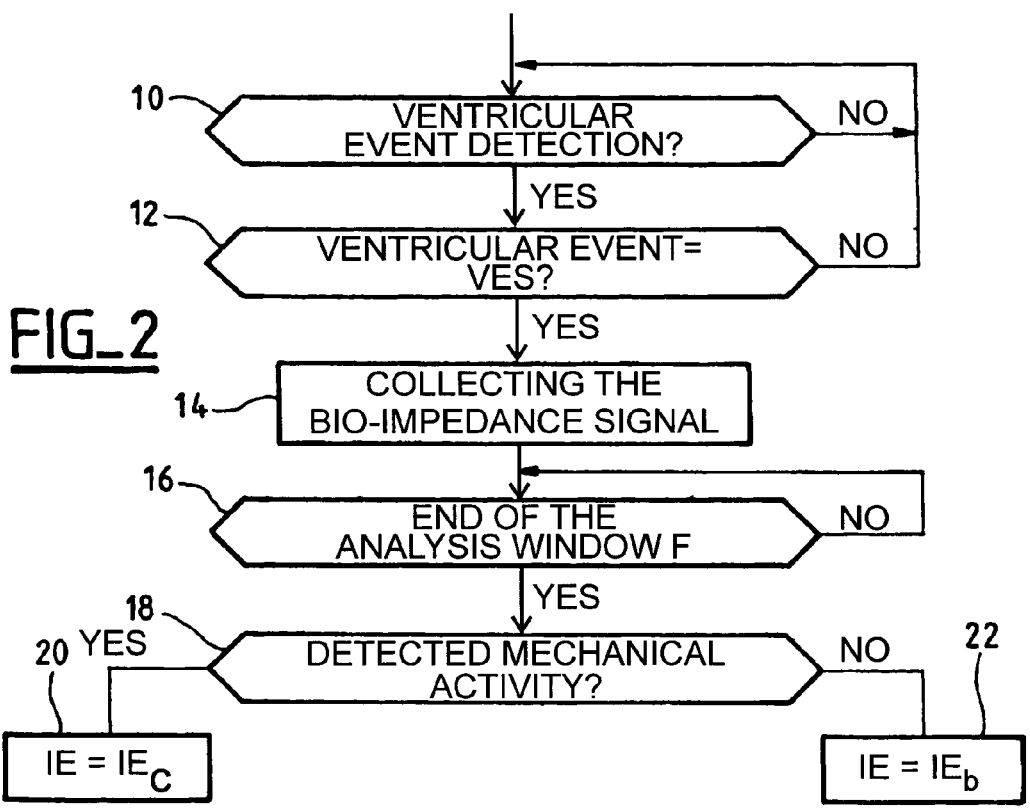
FIG_2

DISCRIMINATION OF NOXIOUS AND NON NOXIOUS VENTRICULAR EXTRASYSTOLES IN AN ACTIVE IMPLANTABLE MEDICAL DEVICE SUCH AS A CARDIAC PACEMAKER, DEFIBRILLATOR, CARDIOVERTOR AND/OR MULTISITE DEVICE

FIELD OF THE INVENTION

The present invention relates to "active implantable medical devices" as such devices are defined by the Jun. 20, 1990 directive 90/385/CEE of the Council of the European Communities, and more particularly to cardiac pacemaker, defibrillator and/or cardiovertor devices that are likely to deliver to the heart pulses of low energy for the treatment of the disorders of the cardiac rhythm. The invention is more particularly directed to the prostheses known as "multisite" devices in which electrodes are placed in a plurality of distinct respective sites comprising at least one ventricular site and one atrial site, for example, a prosthesis of the "double chamber" (right atrial stimulation and right ventricular stimulation) or more generally the "triple chamber" (right atrial stimulation and double ventricular stimulation) or "quadruple chamber" (double atrial stimulation and double ventricular stimulation) type.

BACKGROUND OF THE INVENTION

The invention relates to the consequences of the occurrence of ventricular extrasystoles (VES) on the operation of these implantable devices.

A VES is generally defined as a spontaneous depolarization of the ventricle that was not preceded, in a given interval of time, by an associated spontaneous atrial event (i.e., natural depolarization of the atrium) or stimulated atrial event (i.e., a pulse of low energy delivered by the device to the atrium to cause a depolarization of the atrium). The interval in question is typically an interval defined by a temporal window selected in a range from between 31 and 300 ms preceding the detection of the ventricular activity.

One can also consider that there is a VES when the device detects a ventricular activity that is preceded by an atrial event in an interval of time included in the aforementioned window (e.g., between 31 ms and 300 ms), but with an atrio-ventricular delay (AVD) of the examined cardiac cycle that is less than a given duration (for example, less than 31 ms) to the AVD of the preceding cardiac cycle. The cardiac cycle is defined as the interval of time between two events of a comparable nature in the same cavity.

For further details on the extrasystoles, one will be able to refer to the published EP-A-0 550 342 and its corresponding U.S. Pat. No. 5,312,451, commonly assigned herewith to ELA Médical, which describes an algorithm for the detection and treatment of VES. U.S. Pat. No. 5,312,451 is incorporated herein by reference in its entirety.

In practice, patients present at the basal state a certain number of isolated VES without adverse consequences. But when these extrasystoles become too frequent, the phenomenon can deteriorate the filling of the cavities, and thus the hemodynamic function of the heart. Frequent VES also can facilitate the appearance of disorders of the cardiac rhythm, which may or may not be related to a degradation of hemodynamic performance.

The current pacemakers typically have an associated control algorithm that on detection of a VES will consider that it relates to a cardiac cycle and re-trigger the counting of the various delays, in particular a ventricular escape interval (VEI) that is recycled (i e., starts over). This is done to avoid triggering a ventricular fibrillation by delivering an inappropriate stimulation. But these known devices always react in a systematic and undifferentiated way when they detect a VES.

The starting point of the invention lies in the observations by the inventor that the effects of the VES can be variable, from one patient to another, and also for the same patient from one VES to the next, and that it can be convenient to differentiate how the device responds to a VES according to the foreseeable effects of the detected VES. Indeed, the spontaneous ventricular activity resulting from a given VES can have very variable physiological effects: from the absence of any effect to the blocking of a complete cardiac cycle, with the most frequent intermediate situation being a notable fall in the ejected blood volume, because of a contraction that is of poor quality or out of phase as compared to the remainder of the cardiac cycle.

Thus, for example, when a VES occurs at the end of the systolic phase, i.e., when the myocardium is indeed contracted, the VES will temporarily block this contraction (more specifically, the uncontraction). As a result, there will be no further influx (inflow) of blood into the organ throughout this blocking. For another example, if the VES occurs at a moment when the myocardium is not contracted or only a little contracted, it will cause a mechanical contraction of the cavity involving the expulsion of a blood volume.

One will understand that, to optimize the hemodynamic function of the patient, the next ventricular stimulation will have to intervene at a different moment, according to the situation. This can be obtained, for example, by a suitable adaptation of the VEI used by the pacemaker to define the next moment for stimulation. The VEI is defined as the interval of time, counted after a detection or a stimulation in the ventricle, following which a stimulation is delivered to this same ventricle if no spontaneous event is detected.

OBJECT AND SUMMARY OF THE INVENTION

Thus, it is an object of the present invention to operate, for each detected VES, a discrimination that is likely to determine whether the VES involves a mechanical contraction of the heart, and more preferably to adapt an operating parameter of the device in response to the discriminated VES, for example, an adaptation of the escape interval that is used to define the moment of next ventricular stimulation.

Another object of the invention, in the alternative or as a complement to the differentiated reaction, is a statistical object, with a diagnostic purpose, of counting according to the type of detected VES—while distinguishing between those involving a mechanical contraction (defined herein as "non noxious VES") and the others (the so called "noxious VES", with blocking)—, and then to calculate and memorize (store in memory a suitable parameter), for example, the proportion of noxious VES compared to the total number of VES. This parameter can then be used as a valuable tool for the physician confronted with the study of the rate of the patient, in complement to the frequency of appearance of the VES ("rate of extrasystole"), because it will be able to thus evaluate not only the frequency of the VES, but also their global degree of harmfulness to the patient.

To this end, the present invention proposes, primarily, to record an intracardiac impedance signal in the event of detection of VES, and to evaluate, based upon this signal, the presence or absence of a significant mechanical activity of the heart consecutive to the occurrence of, the invention proposes an improvement to a device of the known type, for example the detected VES.

More preferably, according to that disclosed in the EP-A-0 550 342 and U.S. Pat. No. 5,312,451 mentioned above, i.e., including means for sensing ventricular and atrial cardiac activity and analyzing means responsive to the sensed cardiac activity, for detecting a heartbeat rate and cardiac cycles and an occurrence of a ventricular extrasystole. According to the invention, this device also includes: measuring means for providing a signal corresponding to an intracardiac impedance correlated to the instantaneous blood flow; and discriminating means, responsive to the intracardiac impedance signal, for sensing variations in said signal, determining a presence or an absence of a significant mechanical activity of the myocardium consecutive to a detected ventricular extrasystole, and delivering an indicator of the noxious or non noxious character of the ventricular extrasystole in response to an absence or a presence of said significant mechanical activity of the myocardium, respectively.

In one preferred embodiment, the device also includes a means for modifying in a differentiated manner an operating parameter of the device, in particular the calculated ventricular escape interval, for the cardiac cycle following the detected ventricular extrasystole, in response to the determination, by the discriminating means of the noxious or non noxious character of the detected ventricular extrasystole.

In yet another embodiment, the discriminating means also includes means for evaluating an increased impedance in the intracardiac impedance after an occurrence of a ventricular extrasystole, comparing this increased impedance with a predetermined threshold, and determining a presence of a significant mechanical activity of the myocardium in the event of the crossing of this threshold, i.e., the detected increased impedance is greater than the threshold. The threshold can in accordance with one preferred embodiment be predetermined based upon the value of an initial impedance measured at the time of the occurrence of the ventricular extrasystole, increased by a preset factor of proportionality (i.e., a multiplier).

Preferably, the device also includes a counting means for counting a respective number of noxious and non noxious extrasystoles detected by the analyzing means, and eventually for determining a parameter representative of a relative proportion between the counted noxious and non noxious extrasystoles. It should be understood that the parameter can relate the count of noxious VES to total VES, or the count of non noxious VES to total VES, or form a ratio of noxious to non noxious VES, as the practitioner deems suitable for diagnostic purposes.

BRIEF DESCRIPTION OF THE DRAWINGS

Further benefits, features and characteristics of the present invention will become apparent to a person of ordinary skill in the art in view of the following detailed description of a preferred embodiment of the invention, made with in reference to the annexed drawings, in which:

FIG. 1 is a chronogram illustrating, in addition to the cardiac events markers, an evolution of the electric activity of the ventricle and that of the intracardiac bio-impedance; and FIG. 2 is a flow chart of the various stages of an implementation of the invention.

DETAILED DESCRIPTION OF THE INVENTION

With reference to FIG. 1, illustrated in plot E is an electrocardiographic tracing layout corresponding to a normal cardiac cycle (defined by the event marker P corresponding to a detection of a spontaneous atrial activity and the event marker R corresponding to a spontaneous ventricular activity) followed by a VES stopping this cycle at a moment that, in the illustrated example, is rather late. The late occurrence of this detected VES, during the course of the diastolic phase, will involve a significant mechanical activity (contraction) of the myocardium. It thus concerns a non noxious VES, and in such case it is enough for the device to recycle the escape interval at its normal programmed or calculated value.

One will understand that the term "significant mechanical activity" refers to an activity producing the ejection of a sufficient blood volume so that, from a hemodynamic point of view, the extrasystolic cycle can be compared to a normal cycle, without it being useful or necessary to modify the values of the operating parameters, whether programmed or calculated, of the pacemaker.

On the other hand, if this detected VES had occurred much earlier in time, for example, at the end of the systole, and therefore at the time when the myocardium was indeed contracted, it would not have generated an additional significant mechanical activity. It would, however, have caused the creation of a temporary situation of blocking. In such case, it could then be desirable not only to recycle the escape interval, but also to modify the value of the escape interval to a shorter duration in order to compensate, from the a physiological point of view, the duration of the blocking.

To determine the presence or absence of a significant mechanical activity consecutive to a detected VES, the device evaluates the variations of an intracardiac measurement of bio-impedance after the moment of the occurrence of the detected VES. Indeed, the variations of the measured bio-impedance are closely correlated with the state of contraction of the myocardium. Illustrated on FIG. 1 are the variations of intracardiac impedance Z, in this example a measure of the transvalvular impedance. As one can see, the characteristic of the transvalvular impedance Z presents a maximum corresponding to the end of the ventricular systole, the moment when blood volume is lowest, thus implying a high value of transvalvular impedance.

For the measurement of this transvalvular impedance, reference is made to the EP-A-1 116 497 and its corresponding U.S. Pat. No. 6,604,002 B1, commonly assigned herewith to ELA Médical. These documents describe a technique for measuring the transvalvular bi-impedance (between atrium and ventricle located on the same side of the heart) by a tripolar configuration. A pulse of a current of low amplitude, insufficient to excite the cardiac cells, is injected between two of the sites. A differential potential is sensed between two different sites in this same configuration and provides the impedance signal. U.S. Pat. No. 6,604,002 B1 is incorporated herein by reference in its entirety.

It is known from EP-A-1 138 346 and its corresponding U.S. Published Patent Application US2001/0034540 A1, also commonly assigned herewith to ELA Médical, and incorporated herein by reference, how to obtain a measurement of another type of bio-impedance, namely a transeptal bi-impedance. The transeptal impedance is measured between one site placed on one side of the heart (e.g., the right ventricle) and a site placed on the other side of the heart e.g., the left ventricle or left atrium). This technique also makes it possible to deliver a signal representative of the mechanical activity of the heart. However, the transeptal impedance signal is weaker than in the case of the measurement of a transvalvular bio-impedance, and the delivered signal is also influenced by the impedance of tissues of the septum.

Referring now to FIG. 2, a flow chart illustrates the various stages of a control algorithm that may be implemented by a device in accordance with a preferred embodiment of the invention.

First of all (stage 10), the device waits for an occurrence of a ventricular event. If this ventricular event is a detected VES within the meaning defined above of (stage 12), then the device begins collection (i.e., an acquisition) by digitization and sampling, of an intracardiac impedance signal Z (stage 14). The first or initial intracardiac measurement of impedance, value $Z_0$ (not identified per se in FIG. 2), is used as a reference value for the extrasystolic cycle in progress.

One next defines a threshold S, based on this reference value $Z_0$, for example, a threshold $S=a \cdot Z_0$, with a being a constant multiplier that is greater than 1 (more preferably, a=1.5). One then continues the acquisition of the impedance signal Z throughout a window of analysis F (stage 16). It is during window F that one will search for the presence or absence of a significant mechanical activity of the myocardium.

Mechanical activity of the myocardium results in an increase $\Delta Z$ of the impedance Z quantity. The increased impedance is compared with the threshold S as defined above. The device will then consider (stage 18) that there was significant mechanical activity if the signal Z crosses threshold S. Of course, it should be understood that other thresholds or methods of evaluation of the variation of impedance Z can be used, which technique involves detecting a notable increase in the value of the bio-impedance as compared to an initial measurement $Z_0$.

If the threshold S is crossed, the VES is regarded as non noxious in character and the VEI is maintained at its $IE_C$ value that was previously programmed or calculated (stage 20). This VEI ($IE_C$) is simply recycled from the moment of the occurrence of the VES. The escape interval determined by the device can be, in a way in itself known, a basic escape interval (e.g., a preprogrammed value), or it can be calculated by a control function of the pacemaker, or even by a smoothing or prevention function, or a combination of these functions.

If, at stage 18, the device determines that the impedance signal Z did not exceed the threshold S at the end of analysis window F, this means that the myocardium did not contract or contracted only a little. This will be the case, for example, if the VES occurred at the end of the systole. Such a VES without a consecutive significant mechanical activity is regarded as noxious (and optionally the subject of a specific counting by the device). In addition, the initial value of the VEI is modified for the duration of this extrasystolic cycle with a $IE_b$ value adapted to the situation of blocking created by the VES.

The value of the window of analysis F is in the range of 150 ms after detection of an VES, although this numerical limit is not believed to be limiting or restrictive.

Suitable devices for which the present invention has application include, for example, the active implantable medical devices available from Ela Médical, Montrouge France. These devices are microprocessor-based systems having circuits for receiving, conditioning and processing detected electrical signals, and are capable of receiving software instructions by telemetry, storing them in memory, and then executing those instructions to perform the functions described above in implementing the present invention. The creation of suitable software instructions for controlling an implant to perform the aforementioned functions of the present invention are believed to be within the abilities of a person of ordinary skill in the art. The detection circuits used to detect the cardiac signals in the atrium and the ventricular, in the left and/or right chambers, and to inject currents and measure a bio-impedance in an implantable medical device, are well known and any suitable design may be used.

One skilled in the art will appreciate that the present invention can be practiced by other than the described embodiments, which are presented for purposes of illustration and not of limitation.

I claim:

1. An active implantable medical device comprising:
   means for sensing ventricular and atrial cardiac activity,
   analyzing means for discriminating a ventricular extrasystole from said sensed ventricular cardiac activity, and for detecting in the sensed cardiac activity an occurrence of a cardiac cycle,
   measuring means for delivering an intracardiac impedance signal measured between two cavities of the heart correlated to the instantaneous blood flow, and
   discriminating means for detecting variations in the delivered impedance signal measured between two cavities of the heart, determining, in response to a detected variation, a presence or an absence of a significant mechanical activity of the myocardium consecutive to a discriminated ventricular extrasystole, and determining a noxious character of the ventricular extrasystole in response to a determined absence of significant mechanical activity and a non noxious character of the ventricular extrasystole in response to a determined presence of significant mechanical activity, wherein the discriminating means further comprises means for evaluating an increase in the intracardiac impedance measured between two cavities of the heart after the occurrence of the detected ventricular extrasystole, comparing said increased intracardiac impedance measured between two cavities of the heart to a predetermined threshold, and determining a presence of a significant mechanical activity of the myocardium in response to said increase crossing said threshold.

2. The device of claim 1, wherein the device further comprises an operating parameter associated with controlling a cardiac rhythm and further comprises means for modifying said operating parameter for a cardiac cycle following the detected ventricular extrasystole in a first manner in response to a determined noxious character of the detected ventricular extrasystole and in a second manner for a determined non noxious character of the detected ventricular extrasystole.

3. The device of claim 2, wherein said device further comprises means for calculating a ventricular escape interval and said operating parameter is said calculated ventricular escape interval.

4. The device of claim 1, wherein said measuring means further comprises means for measuring an initial intracardiac impedance measured between two cavities of the heart and measured at the time of the occurrence of the ventricular extrasystole, and said predetermined threshold corresponds to the measured initial intracardiac impedance measured between two cavities of the heart increased by a multiplier greater than one.

5. The device of claim 4, wherein said multiplier is set to 1.5.

6. The device of claim 1, further comprising counting means for counting a number of determined noxious extrasystoles and a number of determined non noxious extrasystoles.

7. The device of claim 6, wherein said counting means further comprises means for determining a parameter representative of a relative proportion of counted noxious and non noxious extrasystoles.

* * * * *